United States Patent [19]

Echigo et al.

[11] Patent Number: 5,716,815
[45] Date of Patent: Feb. 10, 1998

[54] METHOD FOR PREPARING DIMETHYLCARBOXYLIC ACID COMPOUNDS

[75] Inventors: Takashi Echigo; Masahiko Hiramoto; Keijitsu Tanaka, all of Chiba, Japan

[73] Assignee: Showa Denko K.K., Tokyo, Japan

[21] Appl. No.: 670,070

[22] Filed: Jun. 25, 1996

[30] Foreign Application Priority Data

Jun. 26, 1995 [JP] Japan .................. 7-159558

[51] Int. Cl.$^6$ .................. C12P 7/40; C12N 9/02; C12N 1/20
[52] U.S. Cl. .................. 435/136; 435/189; 435/252.1
[58] Field of Search .................. 435/136, 132, 435/252.1, 189

[56] References Cited

U.S. PATENT DOCUMENTS 3,558,431   1/1971   Goodhue et al. .................. 435/136

FOREIGN PATENT DOCUMENTS 52-72882    6/1977   Japan .
54-138886  10/1979   Japan .
62-263141  11/1987   Japan .
 4818827    8/1997   Japan .

OTHER PUBLICATIONS

"Yuki Gosei Kagaku", vol. 36, No. 12 (1978), pp. 1095 to 1100, referred to in the specification, p. 1, lines 21 to 22.
"Derivatives of Pentaerythritol, IV–Identification of By–Products in Pentaerythritol Process Liquors", Liebigs Ann. Chem. 1985, 1082–1087.

*Primary Examiner*—Sandra E. Saucier
*Assistant Examiner*—Susan Hanley
*Attorney, Agent, or Firm*—Sughrue, Mion, Zinn, Macpeak & Seas, PLLC

[57] ABSTRACT

A method for preparing dimethylolcarboxylic acid derivatives represented by general formula (1)

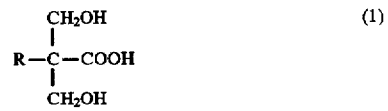

(wherein R is a hydrogen atom, an amino group, an alkyl group, or an alkyl group having a hydroxyl group) to react with a culture broth, cells or a processed cell product of a microorganism belonging to the genus Rhodococcus or Agrobacterium having an ability to oxidize a methylol group of the tris(hydroxymethyl) derivative represented by general formula (2)

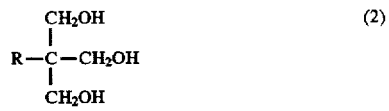

wherein R has the same meaning as defined above.

According to this invention, dimethylolcarboxylic acid derivatives can be produced efficiently under mild conditions by using microorganisms belonging to the genus Rhodococcus or Agrobacterium and having an ability to oxidize tris(hydroxy-methyl) derivatives to produce dimethylolcarboxylic acid derivatives.

13 Claims, No Drawings

METHOD FOR PREPARING DIMETHYLCARBOXYLIC ACID COMPOUNDS

BACKGROUND ART

1. Technical Field

This invention relates to a method for preparing dimethylolcarboxylic acid derivatives, such as 2,2-bis(hydroxymethyl)propionic acid and 2,2-bis(hydroxymethyl) butyric acid, useful as a water-soluble crosslinking agent and a method for preparing dimethylolcarboxylic acid derivatives at high selectivity by oxidation of tris(hydroxymethyl) derivatives using microorganisms.

2. Description of Related Art

As a method for preparing 2,2-bis(hydroxymethyl)carboxylic acid by a chemical process, there have been known, for example, a method in which hydrogen peroxide is used as an oxidizer (Japanese Patent Application Laid-open No. 263141/1987) and a method in which isovaleric peracid is used as an oxidizer (Yuki Gosei Kagaku Kyokai Shi, 36, 1095 (1978)). However, chemical oxidation involves use of oxidizers which are difficult to handle and in addition yield of dimethylolcarboxylic acid derivatives is low.

Another chemical process for preparing dimethylolcarboxylic acid by oxidizing tris(hydroxymethyl) derivatives is a method in which sodium trimethylol acetate is synthesized from pentaerythritol by catalytic air oxidation using platinum and/or palladium as a main catalyst as disclosed in Japanese Patent Application Laid-open No. 138886/1979. This method is uneconomical since it is necessary to use expensive platinum catalysts.

Therefore, it has been expected to develop a method for preparing dimethylolcarboxylic acid derivatives in high yields by oxidation of tris(hydroxymethyl) derivatives using microorganisms.

However, tris(hydroxymethyl) derivatives, which have a neopentane structure not existing in a main metabolic pathway of living organisms, are difficult to undergo biological oxidation.

For example, as the microorganisms that oxidize hydroxymethyl derivatives having a neopentane structure, there have been known only those microorganisms belonging to the genus Flavobacterium (Japanese Patent Publication No. 18827/1973), Corynebacterium or Arthrobacter (Japanese Patent Application Laid-open No. 72882/1977) that oxidize pentaerythritol. However, no microorganism has been known yet that can oxidize tris(hydroxymethyl) derivatives other than pentaerythritol.

Therefore, an object of this invention is to provide a method for preparing dimethylolcarboxylic acid derivatives from tris(hydroxymethyl) derivatives at normal temperature and at normal pressure, safely and inexpensively, in high yields and at high selectivity, by utilizing an ability of oxidizing of microorganisms.

SUMMARY OF THE INVENTION

With view to achieve the above-described object, the present inventors have made extensive research in order to find microorganisms in the natural world that can oxidize tris(hydroxymethyl) derivatives. Although target microorganisms were very difficult to obtain, the present inventors finally succeeded obtaining target microorganism belonging to the genera Rhodococcus and Agrobacterium and found that dimethylolcarboxylic acid derivatives can be prepared from tris(hydroxymethyl) derivatives in high yields and with high efficiency by the use of these microorganisms. This invention has been completed based on this discovery.

That is, this invention provides a method for preparing dimethylolcarboxylic acid derivatives represented by general formula (1)

wherein R is a hydrogen atom, an amino group, an alkyl group, or an alkyl group having a hydroxyl group, comprising allowing tris(hydroxymethyl) derivatives represented by general formula (2)

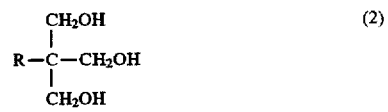

wherein R has the same meaning as defined above to react with a culture broth, cells or a processed cell product of a microorganism belonging to the genus Rhodococcus or Agrobacterium having an ability to oxidize a methylol group of the tris(hydroxymethyl) derivative.

DETAILED DESCRIPTION OF THE INVENTION

The microorganisms which can be used in this invention include microorganisms belonging to the genera Rhodococcus and Agrobacterium having an ability to oxidize methylol groups of tris(hydroxymethyl) derivatives represented by the general formula (2) above.

Table 1 shows characteristics of *Rhodococcus erythropolis* SD806 strain, a typical strain belonging to the genus Rhodococcus from among the microorganisms which can be used in this invention.

TABLE 1

| Characteristics of *Rhodococcus erythropolis* SD806 strain | |
|---|---|
| Morphology | Polymorphic rod |
| Gram stain | + |
| Spore | − |
| Mobility | − |
| Oxidase | − |
| Catalase | + |
| Color of colony | Orange |
| Formation of carotenoid pigment | + |
| Rod-coccus cycle | + |
| Elongation of cells in the periphery of colony | Observed |
| Existence of aerial mycelium | Not observed |
| Behavior toward oxygen | Aerobic |
| Diamino acid in cell walls* | meso-diaminopimelic acid |
| Glycolyl test | + (Glycolyl type) |
| Sugar composition of cell walls* Arabinogalactan polymer | + |
| Mycolic acid | + |
| Quinone | MK-8 ($H_2$) |
| Adenine decomposition | + |
| Tyrosine decomposition | + |
| Urea decomposition | + |
| Assimilability | |
| Inositol | + |
| Maltose | + |
| Mannitol | + |
| Rhamnose | − |

TABLE 1-continued

Characteristics of *Rhodococcus erythropolis* SD806 strain

| | |
|---|---|
| Sorbitol | + |
| m-Hydroxybenzoic acid | − |
| Sodium benzoate | − |
| L-Tyrosine | − |
| Growth in the presence of 0.02% Sodium azide | − |

*Assumed from acid hydrolyzate of whole cell.

In comparison with other strains with reference to "Bergey's Manual of Systematic Bacteriology", Vol. 1 (1984), this strain was characterized by formation of red color colonies, proliferation by multilateral budding, no formation of ascospores, and no fermentation of sugar and thus identified to be *Rhodococcus erythropolis*. The strain was named *Rhodococcus erythropolis* SD806 strain and deposited at National Institute of Bioscience and Human-Technology Agency of Industrial Science and Technology, 1–3, Higashi 1 chome, Tsukuba-Shi, Ibaraki-ken, 305 Japan under Accession No. FERM P-14956 on May 29, 1995 and transferred to International Deposition under Accession No. FERM BP-5521 on Apr. 24, 1996.

Table 2 shows characteristics of Agrobacterium sp. SD807, a typical strain belonging to the genus Agrobacterium which can be used in this invention.

TABLE 2

Characteristics of Agrobacterium sp. SD807 strain

| | |
|---|---|
| Morphology | Rod |
| Gram stain | − |
| Spore | − |
| Mobility | + |
| Flagellum | Peritrichous |
| Behavior toward oxygen | Aerobic |
| Color of colony | Produces no characteristic colony pigment |
| Oxidase | + |
| Catalase | + |
| OF | O |
| Slime formation | + |
| Formation of 3-ketolactose | − |
| Reduction of nitrates | − |
| Reduction of nitrites | − |
| Growth at 35° C. | + |
| Growth at 28° C. | + |
| Growth on Schroth et al selective medium | − |
| Growth in the presence of 2% NaCl | + |
| Production of acids | |
| meso-Erythritol | − |
| Ethanol | − |
| Glucose | + |
| Production of alkalis | |
| Sodium malonate | −* |
| Simons' citric acid agar | − |
| Litmus milk | Oxidation* |
| Liquefaction of gelatin | − |
| Urea decomposition | + |
| β-Galactosidase | + |
| Oncogenesis on stems of sunflower | − |
| Quinones | Q-10 |

*Does not coincide with the characteristics of *Agrobacterium biovar* 3 described in "Bergey's Manual of Systematic Bacteriology", Vol. 1 (1984).

In comparison with other strains with reference to "Bergey's Manual of Systematic Bacteriology", Vol. 1 (1984), this strain was characterized by mobility by peritrichon, gram negative rod, formation of 3-ketolactose, no formation of acids from ethanol, and so on and thus supposed to be *Agrobacterium biovar* 3. However, this strain did not produce alkali from sodium malonate but oxidized litmus milk. Therefore, the characteristics of this strain did not coincide with those of *Agrobacterium biovar* 3 completely and, hence, this strain was not identified.

Accordingly, this strain was named Agrobacterium sp. SD807 strain and deposited at National Institute of Bioscience and Human-Technology Agency of Industrial Science and Technology, 1–3, Higashi 1 chome, Tsukuba-shi, Ibaraki-ken, 305 Japan under Accession No. FERM P-14957 on May 29, 1995 and transferred to International Deposition under Accession No. FERM BP-5522 on Apr. 24, 1996.

The method for preparing dimethylolcarboxylic acid derivatives using the microorganisms according to this invention will be described taking an example of preparation of 2,2-bis(hydroxymethyl)propionic acid from 1,1,1-tris(hydroxymethyl)ethane.

As the microorganism, there can be used also those microorganisms belonging to the genus Rhodococcus or Agrobacterium and having an ability to oxidize the above-described methylol group as well as those microorganisms selected from mutants and/or variants of these microorganisms that have an increased productivity of 2,2-bis(hydroxymethyl)propionic acid.

As such mutants and/or variants, there can be cited mutants and/or variants having an increased resistance to 2,2-bis(hydroxymethyl)propionic acid, mutants and/or variants which do not assimilate 2,2-bis(hydroxymethyl) propionic acid, and the like.

Such mutants and/or variants can be obtained usually by mutation induction treatment of vegetative cells, for example, those cells obtained after incubation in a nutrient medium at 30° C. for 2 to 3 days with shaking. As the mutagen, there can be cited those substances generally known as mutagens, e.g., alkylating agents such as N-methyl-N'-nitro-N-nitrosoguanidine (NTG), base analogs such as 5-bromouracil (5BU), sodium dimethylaminobenzenediazosulfonate (DAPA), azaserine, acridine orange, etc., and ultraviolet rays. In the case of DAPA, cells are treated while they are grown in the presence of nutrition sources. Whereas, in the case of other mutagens or ultraviolet rays, cells are suspended in physiological saline or phosphate buffer solutions before treatment.

With regard to the characteristics relative to productivity of 2,2-bis(hydroxymethyl)propionic acid, mutants and/or variants that have one of such characteristics are effective. However, a considerable increase in productivity can be obtained by the use of variants that have two or more characteristics in combination.

The bacterial strains used in this invention are useful as a source from which genes coding for enzymes relating to oxidation of a hydroxymethyl group in tris(hydroxymethyl) derivatives.

For selecting clones having target genes, a decrease in pH accompanied by production of 2,2-bis(hydroxymethyl) propionic acid from 1,1,1-tris(hydroxymethyl)ethane is used as an index. More particularly, bacterial cells after the treatment are spread on an agar plate medium containing 1,1,1-tris(hydroxymethyl)ethane, suitable nutrition sources and pH indicator and incubated, followed by screening colonies that show changes of color of the pH indicator according to a decrease in pH due to formation of 2,2-bis (hydroxymethyl) propionic acid. Among the clones thus obtained can be found strains having an ability to oxidize tris(hydroxymethyl) derivatives in high frequency.

As the carbon and nitrogen sources in culture media used in this invention for cultivation of microorganisms, there can be used any carbon and nitrogen compounds that the microorganisms can assimilate and grow thereon or therein. Induction of hydroxymethyl group oxidizing enzymes is unnecessary, and immediately after usual cultivation, 1,1,1-tris(hydroxymethyl)ethane or the like can be added to cause oxidation reaction to proceed.

The cultivation can be carried out usually under aerobic conditions at a temperature within the range of 20° to 35° C., preferably 27° to 32° C. While cultivation time may vary depending on the composition of the culture medium and cultivation conditions, usually, cultivation can be carried out for 1 to 3 days. The pH of culture medium is within the range of 6.0 to 8.0, preferably 6.4 to 7.6.

Preparation of dimethylolcarboxylic acid according to this invention may also be performed by a so-called resting cell suspension method in which cells after cultivation are harvested from the culture medium, re-suspended in a buffer solution containing tris(hydroxymethyl) derivatives, and allowed to react therewith. According to this method, separation and purification of dimethylolcarboxylic acid derivatives are easy since the solution contains less components of culture medium and metabolites produced by the cells.

The bacterial cells after cultivation can be harvested by centrifugation or the like. To the cells is added a buffer solution of a mixture of phosphoric acid, acetic acid or the like with its salt or water to suspend the cells. The concentration of the buffer solution is about 50 to 200 mM. The pH of the solution upon reaction is within the range of 6.0 to 8.0, preferably 6.4 to 7.2.

The concentration of a substrate, i.e., a tris (hydroxymethyl) derivative 0.5 to 100 g/l, preferably 5 to 10 g/l. The reaction is carried out under aerobic conditions at a reaction temperature within the range of 20° to 35° C., preferably 27° to 32° C. During the reaction, pH varies according as carboxylic acid is produced and thus pH is desirable to be controlled within the preferred range.

As the tris(hydroxymethyl) derivatives used as substrates for oxidation by microorganisms according to this invention, no limitation is posed as far as they are tris(hydroxymethyl) derivatives represented by general formula (2)

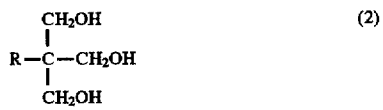

wherein R is a hydrogen atom, an amino group, an alkyl group, or an alkyl group having a hydroxyl group. When R is an alkyl group, the alkyl group contains preferably 1 to 20 carbon atoms, with an .methyl group and an ethyl group being particularly preferred. Further, when R is an alkyl group having a hydroxyl group, R is preferably one which has a carbon chain having 1 to 20 carbon atoms and at least one of the carbon atoms is substituted by a hydroxyl group. A hydroxymethyl group is particularly preferred.

According to the method of this invention, separation and purification of dimethylolcarboxylic acid derivatives which accumulate in the culture medium can be carried out by removing bacterial cells by a conventional method, for example, centrifugation, filtration, membrane separation or the like, followed by ion exchange chromatography or crystallization.

PREFERRED EMBODIMENTS FOR CARRYING OUT THE INVENTION

Hereafter, this invention will be explained concretely by representative examples. However, this invention is not limited to these examples.

Table 3 shows the composition and pH of culture media 1 to 3 used in the examples.

TABLE 3

| Component | Culture Medium 1 | Culture Medium 2 | Culture Medium 3 |
|---|---|---|---|
| Peptone | 10 g | 5 g | — |
| Yeast extract | 5 g | 5 g | 5 g |
| NaCl | 5 g | — | — |
| Water | 1 liter | 1 liter | 1 liter |
| pH | 7.0 | 7.0 | 7.0 |

In the examples, detection and determination of tris (hydroxymethyl) derivatives and dimethylolcarboxylic acid derivatives were carried out by a high performance liquid chromatography using Showdex KC-811 columns.

Example 1

Bacterial cells of *Rhodococcus erythropolis* SD806 strain and Agrobacterium sp. SD807 grown on solid agar media, respectively, each consisting of the culture medium having the composition of culture medium 1 (L broth) shown in Table 3 plus 1.8% agar, mixed with a 50 mM potassium phosphate buffer solution containing 1,1,1-tris (hydroxymethyl)ethane, 1,1,1-tris(hydroxymethyl)propane, pentaerythritol or tris(hydroxymethyl)aminomethane in a concentration of 1% to prepare resting cell suspension reaction mixtures. The reaction mixtures had a turbidity in terms of absorbance of 1.0 at 660 nm. These were shaken at 30° C. for 40 hours for reaction. A portion of the reaction mixture was analyzed by high performance liquid chromatography and as a result, production and accumulation of substances having oxidized hydroxymethyl groups derived from respective substrates were recognized.

Example 2

One loopful bacterial cells of *Rhodococcus erythropolis* SD806 strain were inoculated in 200 ml of a culture medium having the same composition as culture medium 1 shown in Table 3 and incubated with shaking at 30° C. for 2 days. After completion of the incubation, the bacterial cells were harvested by centrifugation and 1 liter of a 50 mM potassium phosphate buffer solution containing 5 g of 1,1,1-tris (hydroxymethyl)ethane was added thereto to prepare a resting cell suspension reaction mixture. The reaction mixture had a turbidity in terms of absorbance of 0.8 at 660 nm. This was shaken at 30° C. for 24 hours. A portion of the reaction mixture was analyzed by high performance liquid chromatography and as a result, it was found that 3.3 g of 1,1,1-tris(hydroxymethyl)ethane was oxidized and decomposed to produce 1.1 g of 2,2-bis (hydroxymethyl)propionaldehyde and 2.0 g of 2,2-bis (hydroxymethyl)propionic acid.

Example 3

One loopful bacterial cells of Agrobacterium sp. SD807 strain were inoculated in 5 ml of a culture medium having the same composition as culture medium 2 shown in Table 3 and incubated with shaking at 30° C. for 1 day. After completion of the cultivation, the bacterial cells were harvested by centrifugation and a 50 mM potassium phosphate buffer solution containing 1,1,1-tris(hydroxymethyl)ethane in a concentration of 5 g/l was added thereto to prepare a resting cell suspension reaction mixture. This was shaken at 30° C. The reaction mixture had a turbidity in terms of absorbance of 0.2 at 660 nm. A portion of the reaction mixture was analyzed by high performance liquid chromatography and as a result, it was found that 4.9 g/l of 1,1,1-tris(hydroxymethyl)ethane had been oxidized at 66 hours of the reaction to produce 0.1 g/l of 2,2-bis(hydroxymethyl)propionaldehyde and 4.8 g/l of 2,2-bis(hydroxymethyl)propionic acid. Conversion rate of 1,1,1-tris(hydroxymethyl)ethane to 2,2-bis(hydroxymethyl) propionic acid was about 88%.

Example 4

One loopful bacterial cells of Agrobacterium sp. SD807 strain were inoculated in 10 ml of a culture medium having the same composition as culture medium 3 shown in Table 3 and at the same time 0.5 g of 1,1,1-tris(hydroxymethyl) ethane was added thereto. During incubation under an aerobic condition at 30° C., absorbance at 660 nm and a change in composition of the reaction mixture with lapse of time were examined. Since pH decreased in accordance with production of 2,2-bis(hydroxymethyl)propionic acid, the reaction mixture was controlled to pH 6.8 with 1N NaOH. The turbidity of bacterial cells at 20 hours of cultivation incubation and reaction increased to 2.0 and thereafter the amount of bacterial cells was substantially constant. The amount of 1,1,1-tris(hydroxyl-methyl)ethane decreased linearly for 30 hours after the initiation of incubation and reaction while 2,2-bis(hydroxymethyl)propionic acid accumulated concomitantly. At 30 hours of cultivation and reaction, 0.4 g of 1,1,1-tris(hydroxymethyl)ethane was oxidized and 0.41 g of 2,2-bis(hydroxymethyl)propionic acid was produced and accumulated. Conversion rate of 1,1,1-tris(hydroxymethyl)ethane to 2,2-bis(hydroxymethyl) propionic acid was about 93%.

Example 5

After being washed with a 50 mM potassium phosphate buffer solution, bacterial cells of Agrobacterium sp. SD807 grown on an L agar medium were added to a 50 mM potassium phosphate buffer solution containing a tris (hydroxymethyl) derivative in a concentration of 5 g/l to prepare a resting cell suspension reaction mixture. This was shaken at 30° C. for 6 hours. The reaction mixture had a turbidity in terms of absorbance at 660 nm of 1.0. After the reaction was over, a portion of the reaction mixture was analyzed by high performance liquid chromatography and rate of production and accumulation of oxides from each derivative was calculated. Table 4 shows the results obtained.

TABLE 4

| Tris(hydroxymethyl) derivative used | Oxidation product | Accumulation of oxide (g/l/hr/OD) |
|---|---|---|
| 1,1,1-Tris(hydroxymethyl)ethane | Dimethylolpropionic acid | 0.65 |
| 1,1,1-Tris(hydroxymethyl)propane | Dimethylolbutyric acid | 0.55 |
| Pentaerythritol | Trimethylolacetic acid | 0.15 |

TABLE 4-continued

| Tris(hydroxymethyl) derivative used | Oxidation product | Accumulation of oxide (g/l/hr/OD) |
|---|---|---|
| Tris(hydroxymethyl)aminomethane | 2,2-Bis(hydroxymethyl)glycine | 0.02* |

*The concentration of oxide accumulated was low since the oxidation products was further assimilated and decomposed.

ADVANTAGEOUS EFFECTS

According to this invention, dimethylolcarboxylic acid derivatives can be produced efficiently and safely by using microorganisms belonging to the genus Rhodococcus or Agrobacterium having an ability to oxidize tris (hydroxymethyl) derivatives to produce dimethylolcarboxylic acid derivatives.

What is claimed is:

1. A method for preparing a dimethylolcarboxylic acid compound represented by formula (1):

wherein R is selected from the group consisting of a hydrogen atom, an amino group, an alkyl group and an alkyl group substituted with a hydroxy group, comprising the steps of:

(A) culturing a microorganism in culture medium comprising a tris(hydroxymethyl) compound represented by formula (2):

wherein R has the same meaning as defined above, or culturing said microorganism, harvesting the resulting cells, and resuspending the resulting cells in a buffer solution comprising a tris(hydroxymethyl) compound represented by formula (2), wherein said microorganism is strain Rhodococcus erythropolis SD806, strain Agrobacterium sp. SD807, or a mutant strain thereof which is capable of oxidizing a hydroxymethyl group of said compound of formula (2); and (B) recovering the resulting dimethylolcarboxylic acid from the culture medium or buffer solution, respectively.

2. The method for preparing a dimethylolcarboxylic acid compound as claimed in claim 1, wherein R is an alkyl group having 1 to 20 carbon atoms.

3. The method for preparing a dimethylolcarboxylic acid compound as claimed in claim 2, wherein R is a methyl group or an ethyl group.

4. The method for preparing a dimethylolcarboxylic acid compound as claimed in claim 1, wherein R is an alkyl group having 1 to 20 carbon atoms having a hydroxyl group.

5. The method for preparing a dimethylolcarboxylic acid compound as claimed in claim 1, wherein said tris (hydroxymethyl) derivative is pentaerythritol.

6. The method for preparing a dimethylolcarboxylic acid compound as claimed in claim 1, wherein said microorganism is strain Rhodococcus erythropolis SD806.

7. The method for preparing a dimethylolcarboxylic acid compound as claimed in claim 1, wherein said microorganism is strain Agrobacterium sp. SD807.

8. The method for preparing a dimethylolcarboxylic acid compound as claimed in claim 1, wherein said culturing or resuspending is carried out at 20° to 35° C. for 1 to 3 days.

9. The method for preparing a dimethylolcarboxylic acid compound as claimed in claim 8, wherein said culturing or resuspending is carried out at 27° to 32° C.

10. The method for preparing a dimethylolcarboxylic acid compound as claimed in claim 1, wherein the pH of the culture medium or buffer solution is in the range of 6.0 to 8.0.

11. The method for preparing a dimethylolcarboxylic acid compound as claimed in claim 10, wherein the pH of the culture medium or buffer solution is in the range of 6.4 to 7.6.

12. The method for preparing a dimethylolcarboxylic acid compound as claimed in claim 1, wherein said compound of formula (2) is present in the culture medium or buffer solution in a concentration of 0.5 to 100 g/l.

13. The method for preparing a dimethylolcarboxylic acid compound as claimed in claim 12, wherein said compound of formula (2) is present in the culture medium or buffer solution in a concentration of 5.0 to 10 g/l.

* * * * *